(12) United States Patent
Melzer et al.

(10) Patent No.: US 8,303,623 B2
(45) Date of Patent: Nov. 6, 2012

(54) OCCLUDER

(75) Inventors: Andreas Melzer, Mülheim (DE); Stefan Michitsch, Essen (DE)

(73) Assignee: Vueklar Cardiovascular Ltd. (GB)

( * ) Notice: Subject to any disclaimer, the term of this patent is extended or adjusted under 35 U.S.C. 154(b) by 905 days.

(21) Appl. No.: 12/298,486

(22) PCT Filed: Apr. 18, 2007

(86) PCT No.: PCT/EP2007/003388
§ 371 (c)(1),
(2), (4) Date: Mar. 2, 2009

(87) PCT Pub. No.: WO2007/124862
PCT Pub. Date: Nov. 8, 2007

(65) Prior Publication Data
US 2009/0204133 A1    Aug. 13, 2009

(30) Foreign Application Priority Data

Apr. 27, 2006 (DE) .................. 10 2006 020 250
May 10, 2006 (DE) .................. 10 2006 022 000
Aug. 3, 2006 (DE) .................. 10 2006 036 649

(51) Int. Cl.
*A61B 17/08* (2006.01)

(52) U.S. Cl. ........................................ 606/213

(58) Field of Classification Search ............ 600/31; 604/41, 42; 606/157, 158, 213, 215, 232
See application file for complete search history.

(56) References Cited

U.S. PATENT DOCUMENTS 5,451,235 A * 9/1995 Lock et al. ................. 606/213
6,280,385 B1 8/2001 Melzer et al.
6,767,360 B1 * 7/2004 Alt et al. ..................... 623/1.15
6,847,837 B1 1/2005 Melzer et al.
2002/0099437 A1 7/2002 Anson et al.
2006/0212047 A1 9/2006 Abbott et al.

FOREIGN PATENT DOCUMENTS

| DE | 19746735 A1 | 4/1999 |
| EP | 1046375 A1 | 10/2000 |
| EP | 0959777 B1 | 7/2005 |
| EP | 1266606 B1 | 10/2005 |
| WO | 9912478 A1 | 3/1999 |

OTHER PUBLICATIONS

Published International Search Report; International Application No. PCT/EP2007/003388; International Filing Date: Apr. 18, 2007; Date of Mailing: Nov. 28, 2007; 10 pages.
European Search Report; European Application No. 09 00 0066; Date of Mailing Feb. 15, 2012; 2 Pages.
DE 19746735 (A1), Publication Date: Apr. 15, 1999, Abstract Only, 2 Pages.

* cited by examiner

*Primary Examiner* — Ryan Severson
*Assistant Examiner* — Jonathan W Miles
(74) *Attorney, Agent, or Firm* — Cantor Colburn LLP

(57) ABSTRACT

An occluder (7) for sealing body orifices (6, 6a) of the human or animal body is illustrated and described, in particular an occluder (7) for percutaneous transcatheter sealing of atrium septum defects of the human or animal heart (1). According to the invention it is provided that the occluder (7) or parts of the occluder (7) form an electric oscillating resonance circuit, whereby at least one conductive loop forming the inductivity of the oscillating resonance circuit is provided and the occluder (7) or parts of the occluder (7) are formed by the conductive loop.

16 Claims, 13 Drawing Sheets

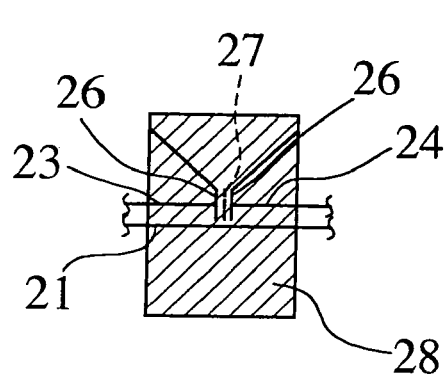 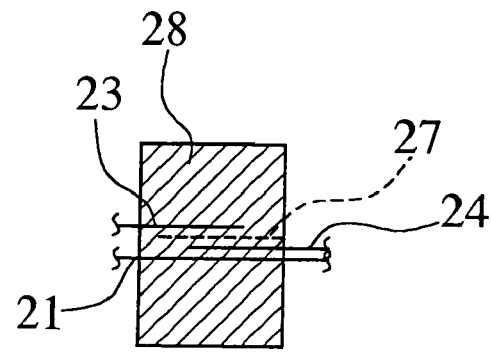
Fig. 8    Fig. 9
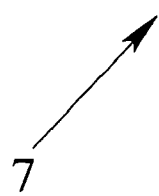
Fig. 10

OCCLUDER

BACKGROUND

The invention relates to an occluder for sealing body orifices of the human or animal body, in particular an occluder for percutaneous transcatheter sealing of atrial septal defects of the human or animal heart.

The foramen ovale is an orifice in the septum between left and right heart atrium in the foetus and the newborn. As a general rule the gap closes over in the first few months of life. In some 20% of humans however this closure is incomplete, leaving a small orifice. This persistent foramen ovale has no effects on the state of health and is accordingly not noticeable to the person concerned. Under certain circumstances it does foster the advent of an apoplectic stroke. Because the open foramen enables blood to shift from the right to the left atrium it can eventuate that a blood clot washed out of a leg vein thrombosis directly enters the arterial circulation via the left atrium and thus possibly reaches the brain. Normally, it would be first sent from the right heart compartment to the pulmonary circulation and filtered out in the lung.

For sealing off septum or vessel defects occluders are used which can be positioned and activated with a catheter. An occluder of the abovedescribed type is known for example from EP-B1-0 959 777. The purpose of occluders is e.g. to seal a persistent foramen ovale (PFO) or an atrium septum defect, for example of secundum type (ASD II [atrial septal defect]). Implanting proceeds as follows. The operator pushes a catheter in from the groin through the vena cava inferior into the right heart atrium and from there through the open foramen ovale into the left atrium. Occluders from the prior art are known, which are folded up like a double umbrella and can be transported by the catheter. A shield-like closure body of the occluder is opened at the target site in the left atrium. The catheter is then withdrawn into the right atrium and a second shield-like sealing body of the occluder is opened. As a result, the occluder lies on both sides of the atrium septum. After becoming overgrown by the inner skin of the heart the foramen ovale is permanently sealed.

With the previously described implant process intervention under X-ray vision and in parallel to this transoesophageal echocardiography (TEE) take place: A sound head placed in the oesophagus generates images of the adjacent heart. At the same time the operator is presented with magnetic resonance (MR) images produced prior to the procedure. MR monitoring of the implanting of an occluder is only very limited or not even possible. The occluder gives rise to image artefacts, whereby these are in particular susceptibility artefacts and so-called RF artefacts (radiofrequency artefacts). Susceptibility artefacts are attributable to the fact that the occluder has greater susceptibility than human tissue. RF artefacts are created by RF excitation pulses. In the process electric currents are induced by the time-variable magnetic field components of the RF pulses in the occluder. These artefacts are gaining significance in particular with occluder materials such as nitinol or tantalum. As a result, an X-ray process for image display during implanting of the occluder cannot be omitted, with the known drawbacks to such methods.

BRIEF DESCRIPTION

The aim of the present invention is to provide an occluder of the type initially mentioned, which can be displayed clearly and signal-intensively in the MR image.

To solve this task it is provided in an occluder of the abovementioned type that the occluder or parts of the occluder form an electric oscillating resonance circuit, whereby at least one conductive loop forming the inductivity of the oscillating resonance circuit is provided and the occluder or parts of the occluder are formed by the conductive loop. According to the invention there is provision to use only one structure, specifically a conductive loop, both for forming the actual occluder and also for inductivity. An oscillating resonance circuit is thus provided in combination with capacitance. An occluder, which is designed as an oscillating resonance circuit, improves viewing of the implant in an MR image, whereby the resonance frequency of the resonant circuit substantially preferably equals the resonance frequency of the radiated RF radiation of the MR imaging system. This contributes to a clear decrease in RF artefacts. As a result, the implanting of the inventive occluder can be monitored readily and without mandatory use of an X-ray process with an MR procedure. The occluder has according to the invention at least one closed resonant circuit with inductivity and capacitance, whereby this system has a varying signal response which can be detected and displayed localized by at least one receiver coil.

The inventive occluder is preferably provided for sealing septum or vessel defects. It is understood that the occluder can also basically be used for sealing any wall defects in hollow organs of the human or animal body. In particular, the inventive occluder can be used for sealing a persistent atrium septum defect, in particular a persistent foramen ovale (PFO) or an atrium septum defect of secundum type (ASD II). Also, ventricle septum defects (VSD) can be sealed using the inventive occluder. Finally, the occluder can also be used for example to seal fistulas. The occluder can further be provided for sealing a persistent ductus arteriosus (Ductus-Botalli).

In a preferred first embodiment of the inventive occluder at least two opposite closure bodies arranged at least in certain areas on opposite sides of the body orifice in the state of closure of the body orifice and at least one intermediate piece joining together the closure bodies can be provided, whereby the intermediate piece at least in certain areas is guided in through the body orifice in the state of closure. The intermediate piece easily enables anchoring of the occluder in a wall defect, whereby the closure bodies acting from both sides on the defective wall parts enclosing the wall defect result in the wall parts growing together in the state of implanting of the occluder.

In another second embodiment of the invention it can be provided that at least one inner closure body is provided arranged inside the body orifice in the state of closure of the body orifice. The above second embodiment is employed in particular for tubular body orifices which extend over a sufficient length. It is understood in the case of the latter embodiment that in addition to the closure body arranged inside the body orifice other closure bodies can be provided which are arranged on opposite sides of the body orifice and act against the defective wall parts in the implanting or respectively state of closure of the occluder. The closure bodies arranged in front of and behind the body orifice exert pressure on the wall parts enclosing the wall defect and support the therapeutic function of the inlying closure body.

With the abovementioned first and second embodiments the closure body can be equipped with a tissue casing, a (metal) coating or a film to support sealing the body orifice through stimulation of tissue growth inside the body orifice or respectively in the canal of the defect and/or to fulfil a filtering function.

In terms of the invention "closure body" is understood in the case of the abovementioned first embodiment to mean a preferably shield-like, annular, discoid or also flower-like (surface) element or respectively a frame part which in the state of closure lies on one side of the orifice against the body walls enclosing the body orifice (defects). It is understood that the closure body can basically also have other cross-sectional forms. The closure body can also be composed of several segments, whereby a closure body in the first embodiment in each case includes the total of all segments provided on a wall side.

In an embodiment of the invention the occluder forms one or more oscillating resonance circuits in each case with at least one conductive loop, for example resulting in the occluder being able to be operated and detected with several different MR frequencies. It can also be provided that a number of oscillating resonance circuits is interconnected. In addition, the conductive loop can be encased with a non-conductor, in particular plastic and/or ceramic. This contributes to greater stability through increased mechanical stability and trouble-free functioning of the occluder. In a particularly preferred embodiment insulation can be provided to reduce and regulate parasitic capacitance, whereby insulation can also be used for fine-tuning the resonance frequency. The insulation layer or respectively the sheathing can form internal capacitance in connection with at least one conductive loop at the same time.

The oscillating resonance circuit preferably has a resonance frequency, in particular in the high-frequency range, which corresponds to the frequency of an external magnetic field, in particular the Larmor frequency of an MR tomograph. This ensures that the inventive occluder in an MR imaging system can be displayed well, enabling implanting and also the sealing function of the occluder to easily be monitored. It is understood that the resonant circuit basically can also have a resonance frequency in another frequency range.

The conductive loop can have at least one electrically non-conductive material, to the surface of which at least one conductive material, in particular gold, platinum, tantalum and/or a conductive alloy, can be applied. Coating the occluder with a particularly conductive material, such as e.g. gold, improves the development of resonance. In place of gold platinum or tantalum can also be used for coating the occluder, with tantalum having electrochemical compatibility. It is also understood that several layers of insulator and conductor can be applied to the conductive loop. A thin layer of a bonding agent can be applied to the occluder, which improves bonding of the electrically conductive material on the occluder. In another embodiment it can be provided that selective coating of the occluder with an electrically conductive material, in particular with gold or platinum, is provided to form inductivity of the resonant circuit.

As already mentioned, the inventive occluder can have several conductive loops. This enables greater flexibility in shaping the occluder and can further improve resonance. The conductive loops can be connected to one another electrically conductively. In this context the term "conductive loop" is understood to mean a conductor comprising a single piece.

According to the invention it can be provided that at least one closure body is formed by the conductive loop. The occluder is preferably formed by a conductive loop which forms the inductivity of the resonant circuit.

In addition, it is preferably provided that the conductive loop forms a capacitance of the oscillating resonance circuit. By way of example, a condenser can be made by parallel sections of the conductive loop. Alternatively, it is basically also possible, of course, for the condenser to be formed by a separate structural element, such as for example an SMD condenser, integrated into the occluder.

The added disadvantage of the occluder known from EP-B1-0 959 777 is that in the state of closure the shield-like closure bodies in the edge region stand out from the body walls. At these points blood clots can form increasingly which can pose a threat to the health of the patient. Since the closure bodies in the known occluder do not lie fully on the body walls, this makes it difficult for the closure body to be overgrown by skin, meaning that full sealing of the body orifice is not ensured under certain circumstances.

The aim of the present invention is therefore also to provide an occluder of the abovementioned type, which guarantees secure and complete sealing of a body orifice.

The abovementioned task is solved for an occluder of the abovementioned type by a one-sided connection being provided between the intermediate piece and each closure body, whereby the intermediate piece is connected eccentrically to each closure body in the edge region of the closure body in the state of closure and whereby the opposite closure bodies in the state of closure arranged on opposite sides of the body orifice are connected on opposite sides to the intermediate piece. The inventive occluder preferably has two closure bodies, whereby basically also more than two closure bodies can be provided and a closure body can have several segments, where required. In terms of the invention the expression "closure body" is understood to first mean all segments which are provided on one side of the body orifice in the state of closure to effect sealing of the body orifice on this side. The closure bodies exert pressure on the defective wall parts of the septum or vessel defect, resulting in the wall parts growing together, without the need to provide a tissue casing for the occluder. A tissue casing can specifically result in cicatrisation and trigger unwanted tissue reactions.

The closure body is intended to be connected to the intermediate piece at least on one side in the edge region, ensuring a particularly good arrangement of the closure body against the body walls enclosing the body orifice after implanting of the occluder. The one-sided connection provided on the edge side with the intermediate piece ensures slight deformability of the closure body relative to the intermediate piece, such that the closure body can readily adapt to the position of the body wall in the vicinity of the body orifice. This makes fixing the occluder in the body orifice easier and ensures extensively complete arranging of the closure body on the body walls.

The intermediate piece can have for example rectangular gradation with at least two opposite legs or pairs of legs, whereby each leg or respectively each pair of legs is connected at its free end to a closure body. The distance between the closure bodies in the state of closure is thus ascertained by the height of gradation. It is understood that the gradation or development can also exhibit an angle of more or less than 90°, making it easier to lay the closure bodies on the body walls and to seal the body orifice. In addition, the intermediate piece can also have a bend or a loop. The intermediate piece can be provided with an S-shaped profile or also a straight profile, whereby the intermediate piece is provided as a diagonal web between the opposite closure bodies and is connected to the closure bodies on opposite sides in the edge region. Both legs or respectively pair of legs of the intermediate piece can have the same length such that in the state of closure the gradation is arranged substantially centrically to the closure bodies. This improves the fixing of the occluder in the body orifice, whereby the intermediate piece is guided in through the body orifice in the vicinity of gradation. If the closure body is formed annularly and encases a circular (sealing) area the length of the leg or legs connected to a closure body of the intermediate piece can substantially correspond to the radius of the circular area.

To enable an extensively complete arrangement of the closure bodies against the body walls it is preferably provided that the closure bodies are arranged successively substantially in the direction of the body orifice. In another embodiment it can also be provided that the closure bodies are arranged offset to one another to the side. The degree of overlap of the closure body is determined for example by the length of the legs connected to the closure body of the intermediate piece, such that the degree of overlap ultimately also depends on the form of the intermediate piece. This allows the occluder to easily adapt to the form of the body walls and causes both closure bodies to be pressed against the body walls.

The occluder or respectively the conductive loop forming the occluder or parts of the occluder is preferably formed to be ductile such that in the stretched state the occluder can be implanted by means of a catheter and can be unfolded during implanting or when it reaches the target site. This facilitates the implant procedure. In this respect the closure bodies and the intermediate piece can be formed from a one-piece wire made of shape memory alloy or cut from a pipe made of shape memory alloy. The final shaping may require heat treatment. The closure body and the intermediate piece as a result comprise one material piece, enabling simple and cost-effective production, and simplifying implanting by means of catheters. The closure body and the intermediate piece can be made for example by multiple lengthways cutting of a pipe, in particular a nitinol pipe, and subsequent expansion. In the process, pipe sections form both opposite closure bodies. If the occluder forms an electric oscillating resonance circuit a central pipe section can be separated to form a conductive loop and reassembled by means of electric insulation to form the capacitance of the oscillating resonance circuit, to be explained hereinbelow in greater detail.

Using a shape memory alloy makes it easy to stretch the occluder into a long-drawn-out form for implanting by means of a catheter. When it is released the occluder deflects into the sealed position. Secure fixing of the occluder in the orifice after unfolding of the closure body is enabled by the shape memory, whereby the closure bodies are pressed against the body walls in the vicinity of the body orifice due to the deformation forces determined by the shape memory. If the closure bodies form coils of an oscillating resonance circuit formed by the occluder a local excessive increase in signal can already be restored following partial folding of the occluder. By way of example, the proximally laid closure body can give a signal response after unfolding in the left atrium, whereby implanting or respectively alignment of the occluder in the body orifice can be substantially eased.

In order to ensure secure fixing of the occluder in the body orifice it can be provided that the occluder is formed by a one-piece wire converging at its ends, whereby the wire is deformed at opposite points in each case into a wire ring forming an outer closure body, whereby the wire ring has two converging wire sections, whereby the wire sections are bent radially in the direction of the midpoint of the wire ring and merge into legs running parallel to one another and whereby the legs of both closure bodies form the inner intermediate piece. This guarantees simple production of the occluder, whereby for the sake of simplicity the legs of both closure bodies can be connected to one another in the vicinity of the intermediate piece, in particular in the vicinity of the gradation. As a result, on both sides of the gradation respectively the intermediate piece has a pair of legs which at the free end respectively merges into the wire ring forming a closure body. The pair of legs can be soldered, welded or stuck in the vicinity of the gradation.

The free ends of the wire forming the occluder can form or contain a condenser of the oscillating resonance circuit. The capacitance belonging to the oscillating resonance circuit can be made in the form of a plate condenser, whereby two opposite plates can be attached at both free ends of the wire. Alternatively, the capacitance belonging to the oscillating resonance circuit can be in the form of two closely adjacent wire sections, whereby both free ends of the wire are guided over a predetermined length and a predetermined distance parallel to one another. It is just as possible that the capacitance belonging to the oscillating resonance circuit is formed by closely opposite ends of the wire or respectively their cross-sectional area, whereby both opposite wire ends can be arranged parallel and at minimal distance from one another. It is understood that parasitic capacitances can furthermore be formed by parallel wire sections.

The closure body encloses a closure surface or respectively plane, whereby the legs forming the intermediate piece can preferably be arranged to run outside the closure surface. This can substantially rule out disruption to the inductivity formed by the closure body.

At least one closure body and/or the intermediate piece and/or the occluder can be sheathed or respectively encased in tissue. Reference can be made here to artificial tissue known per se from the prior art, preferably tissue made of polytetrafluoroethylene or polyester or tissue available under the brand name Dacron®. The tissue sheathing can also be a metal tissue or a metal network. Sheathing using a film or coating in metallic thin film of a highly tissue-compatible metal is also possible. Using the tissue the occluder can fulfil a filtering function, whereby thrombi remain hanging on the tissue. In addition, sealing of the body orifice is improved by the tissue and growing body tissue on the closure bodies is made easier. Finally, the type and arrangement of the tissue casing can influence on the capacitance of an oscillating resonance circuit formed by the occluder.

The intermediate piece can be encased preferably in the vicinity of the gradation, thus making implanting of the occluder easier and reinforcing skin growth. A scaffold of biocompatible perforated plastic can be provided here. In addition to this, the sheathing can have a guide aperture for a guide wire, enabling the occluder to be threaded into the body orifice during the implant procedure.

In a further advantageous embodiment the occluder has at least one hook-shaped or eyelet-shaped application section for an implant instrument. The application section can be provided by a section formed as torsion spring or as eyelet of a wire piece forming the occluder, or separate structural elements can be used which are connected to the occluder. The application section enables coupling of the occluder to a tool for implanting in the stretched state by means of a catheter or for unfolding the occluder. This allows the operator to handle the occluder easily. In addition, the application section can be provided as guide for a guide wire, with which the occluder can be threaded into the body orifice. The application section can also be provided for withdrawing the partly or fully unfolded occluder, for example when the occluder is recovered.

The wire piece forming the occluder can be formed on folding or bending points as a torsion spring, thus contributing to considerable dimensional stability of the inventive occluder. The torsion springs can also simplify stretching and unfolding of the occluder.

In addition, the invention allows the intermediate piece likewise to fulfil a sealing or centring function when the body orifice is sealed off. In this context it is provided that the intermediate piece has a shape formed for sealing the body orifice and/or for centring and/or for anchoring the occluder in the body orifice. This can mean for example that the intermediate piece has at least one torsion spring, whereby another closure surface is preferably stretched by the torsion spring, which is arranged substantially parallel to a closure surface stretched by a closure body as such and thus substantially in the plane of the defective wall parts. When in the implanting state the torsion spring of the intermediate piece is then arranged inside the body orifice, whereby the occluder is anchored by the torsion spring in the body orifice and centred, where required. In addition, the torsion spring can fulfil a sealing function. Further advantages emerge whenever the intermediate piece has means which facilitate anchoring in the body orifice, for example outer cogging. Appropriate forming of the intermediate piece can ensure that the above-mentioned functions are fulfilled. By way of example, the intermediate piece can extend in the longitudinal direction of the body orifice and have tapering in the middle, which likewise results in centring of the occluder in the body orifice. The intermediate piece can fulfil the function of another closure body which cooperates with the closure bodies of the occluder arranged in front of and behind the wall defect to cause or respectively to support the most complete possible sealing of a septum or vessel defect.

In detail there is a plurality of possibilities for configuring and further developing the inventive occluder, whereby on the one hand reference is made to the dependent patent claims and on the other hand to the subsequent detailed description of a preferred embodiment of the invention with respect to the diagram. The invention also allows where necessary the characteristics mentioned in the claims and/or the characteristics disclosed and described by means of the diagram to be combined with one another, also whenever this is not described in detail, in which:

BRIEF DESCRIPTION OF THE DRAWINGS

FIG. 8 shows a first embodiment of a conductive loop forming capacitance of an occluder in a partial sectional view, FIG. 9 shows another embodiment of a conductive loop forming capacitance of an occluder in a partial sectional view, FIG. 10 shows the occluder illustrated in FIG. 3 in a long stretched-out state.

DETAILED DESCRIPTION

Figure 1:
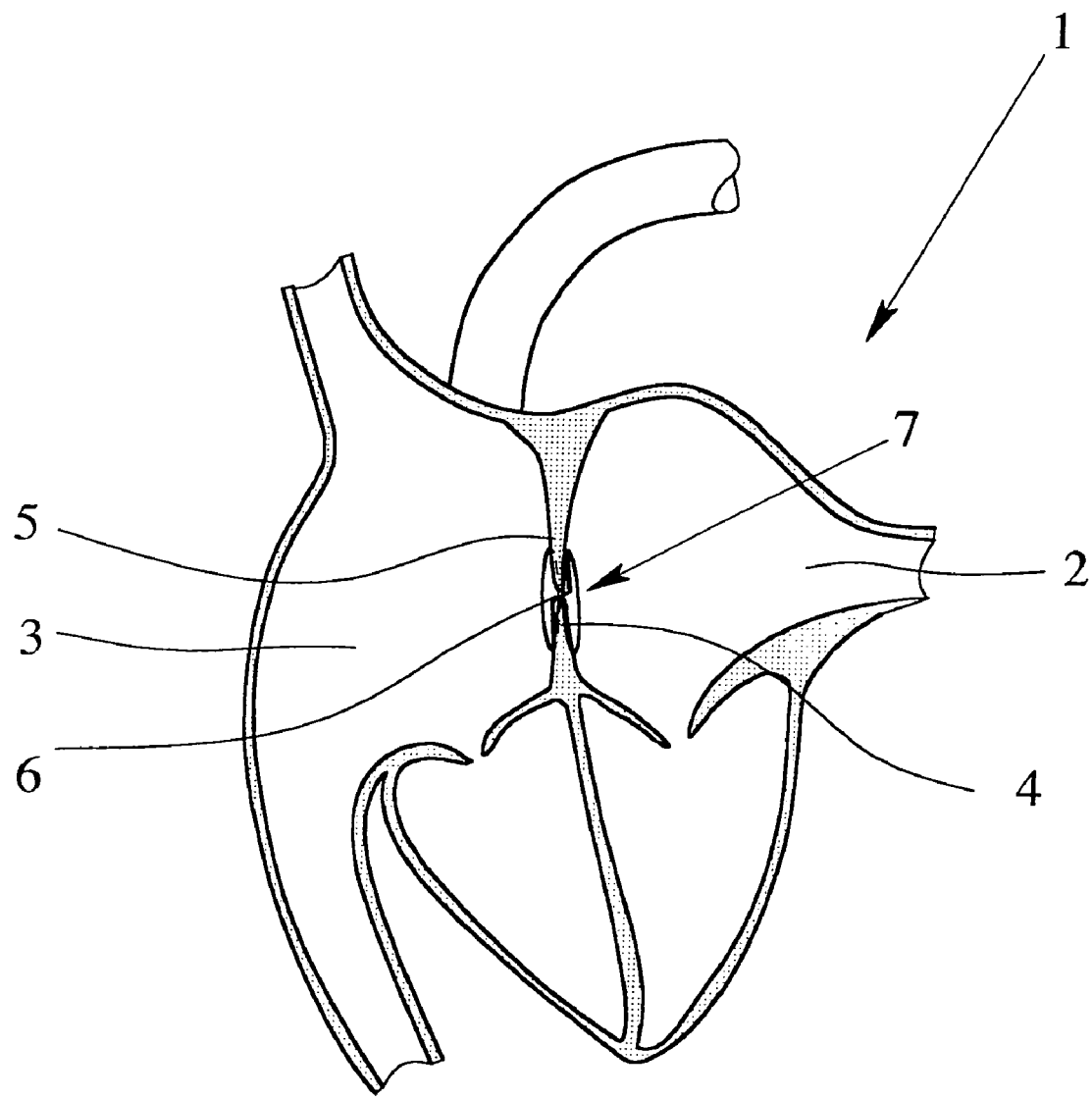
FIG. 1 shows a schematic cross-sectional view of an atrium septum defect of the human heart closed by an occluder.

In FIG. 1 an atrium septum defect (ASD) of a human heart 1 is illustrated, whereby the heart 1 has a left atrium 2 and a right atrium 3. The left atrium 2 and the right atrium 3 are separated from one another by the septum primum 4 and the septum secundum 5. A body orifice 6, the so-called foramen ovale, is illustrated between the septum primum 4 and the septum secundum 5. As a general rule the orifice 6 closes over in the first months of life. In approximately 20% of people however this sealing remains incomplete. This persistent foramen ovale has no effects on the state of health and as a rule is not noticeable to the person concerned, but in some cases does not remain totally without consequences, however. The occurrence of an apoplectic stroke can under certain circumstances be more likely. An occluder 7 which is placed by means of a catheter in the vicinity of the orifice 6 can be used to seal off the body orifice 6, which generally can be a septum or vessel defect.

Figure 2:
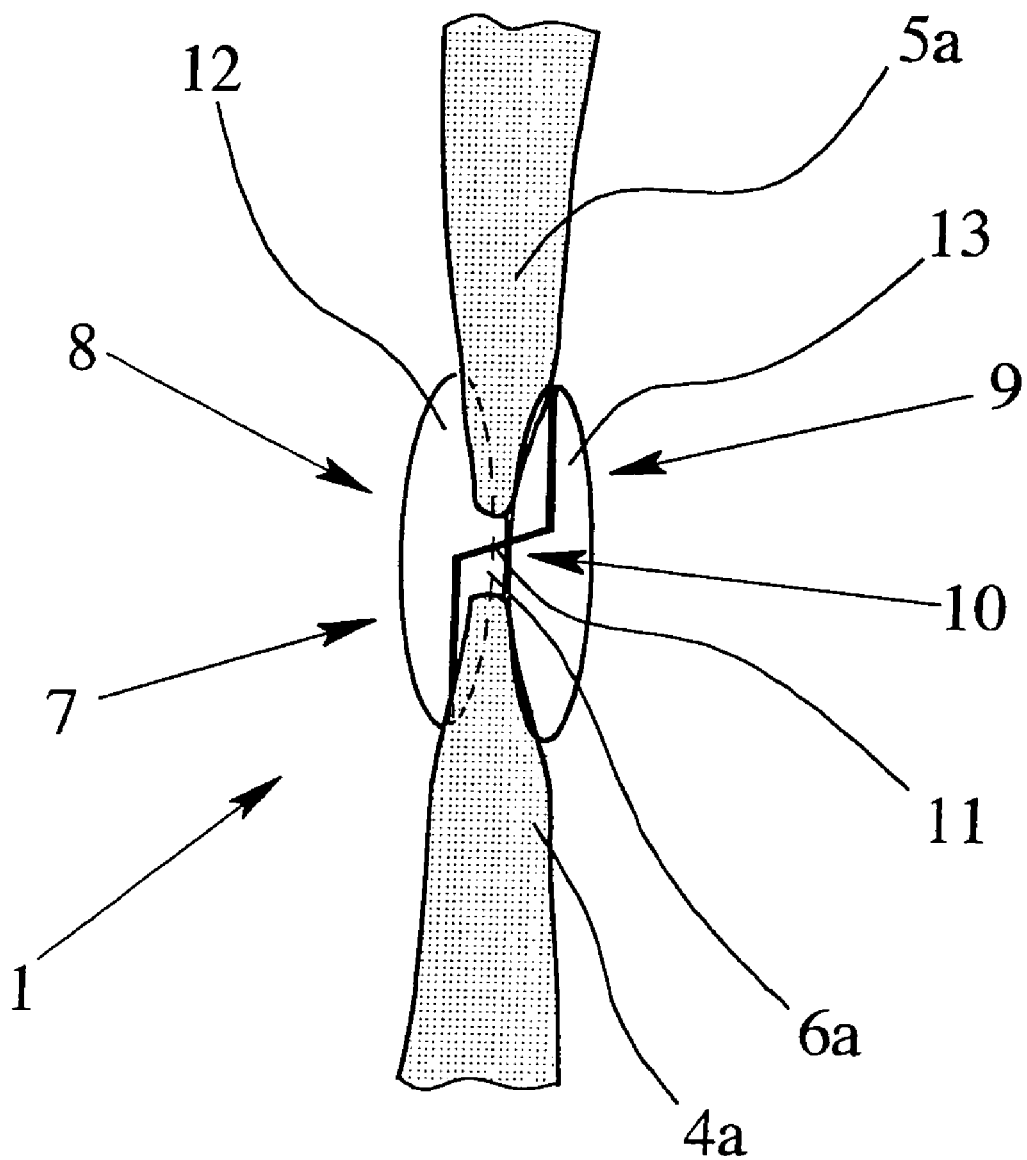
FIG. 2 shows a wall defect closed by an inventive occluder in a schematic cross-sectional view.

FIG. 2 illustrates a wall defect of a body cavity with defective wall parts 4a, 5a, in which an orifice 6a is sealed by an occluder 7. In the state of closure of the body orifice 6a the occluder 7 has annular closure bodies 8, 9 arranged on opposite sides of the body orifice 6a at least in certain areas opposite. The closure bodies 8, 9 are connected to one another by an intermediate piece 10, whereby the intermediate piece 10 is guided in through the body orifice 6a in the vicinity of a gradation 11. In the illustrated embodiment the occluder 7 lies with the annular closure bodies 8, 9 against the body walls which grow over with tissue after implanting of the occluder 7, resulting in complete sealing of the body orifice 6a. The closure bodies 8, 9 frame closure surfaces 12, 13 and can be sheathed in a tissue casing to facilitate tissue growth.

Figure 3:
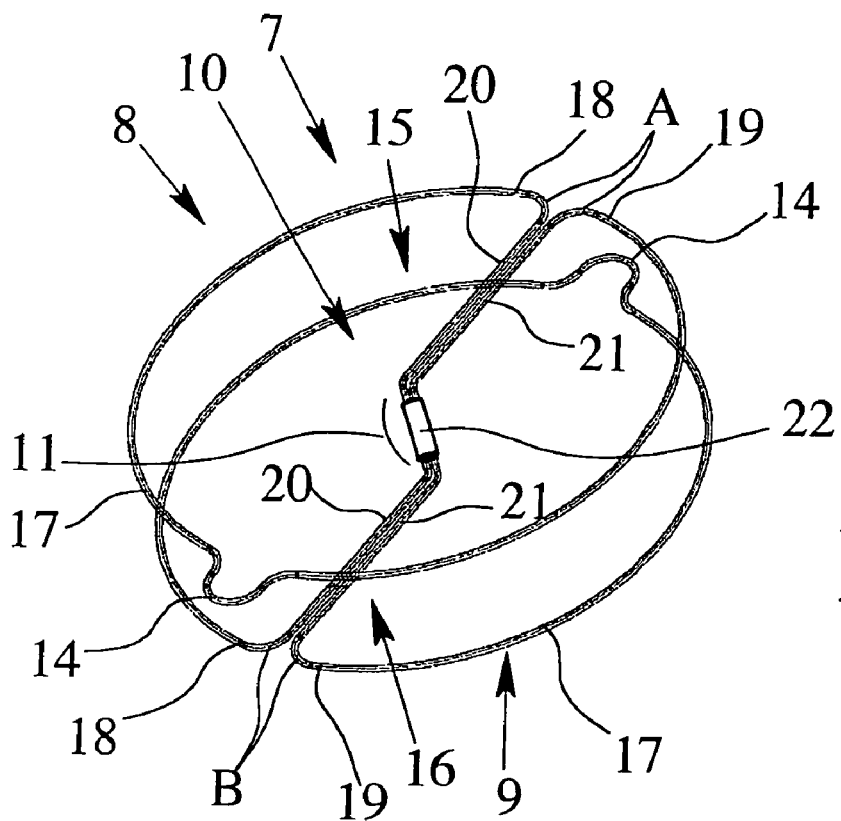
FIG. 3 shows a perspective illustration of an inventive occluder in the unfolded state.
Figure 4:
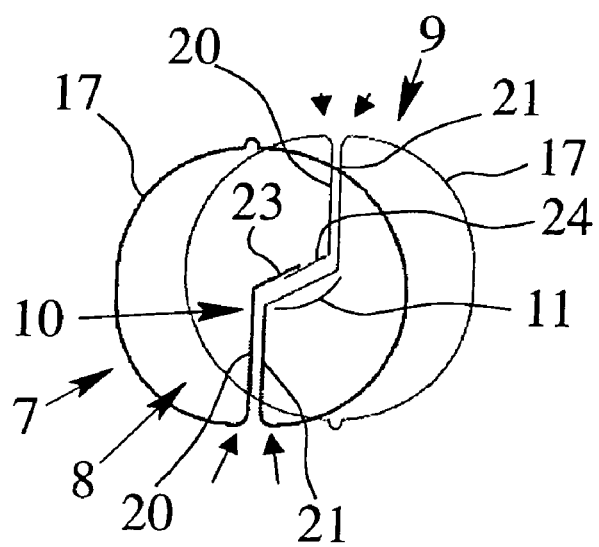
FIG. 4 shows a schematic plan view of a second embodiment of an inventive occluder.

FIG. 3 illustrates a preferred embodiment of the inventive occluder 7 in a perspective view. As is evident from comparison of FIGS. 3 and 10 the occluder 7 can be transferred by stretching into a long stretched-out form, enabling easy implanting of the occluder 7 with a catheter. In order to feed the occluder or respectively to fold the occluder 7 into the stretched state hooked application sections 14 are provided on both closure bodies 8, 9.

The occluder 7 illustrated in FIG. 3 has a one-sided connection between the intermediate piece 10 and the closure bodies 8, 9, whereby in the state of closure the intermediate piece 10 is connected to every closure body 8, 9 eccentrically in the edge region of the closure bodies 8, 9 and whereby the opposite closure bodies 8, 9 arranged in the state of closure on opposite sides of the body orifice 6 are connected on opposite sides A, B to the intermediate piece 10. This ensures that after implanting the occluder 7 lies substantially completely against the body walls enclosing the body orifice 6 with both closure bodies 8, 9. Single-sided fastening of the closure bodies 8, 9 to the intermediate piece 10 enables the closure bodies 8, 9 to adapt very well to the body-specific form of the body walls.

The intermediate piece 10 has a gradation 11 with two opposite running pairs of legs 15, 16, whereby each pair of legs 15, 16 is connected by its free end to a closure body 8, 9. The pairs of legs 15, 16 of the intermediate piece 10 have the same length, such that in the state of closure the gradation 11 is arranged substantially centrically to the closure bodies 8, 9 arranged on opposite sides of the body orifice 6. This makes secure positioning of the closure bodies 8, 9 against the body walls easier and ensures fixing of the occluder 7 in the body orifice 6.

In the embodiment illustrated in FIG. 3 the occluder is formed by a one-piece wire 17 converging at its ends, whereby the wire 17 is deformed at opposite points in each case into a wire ring forming an outlying closure body 8, 9. The wire ring has two converging wire sections 18, 19, whereby the wire sections 18, 19 are bent out radially in the direction of the central point of the wire ring and merge into common legs 20, 21 running parallel to one another. The legs 20, 21 form the pair of legs 15, 16 on both sides of the gradation 11. The intermediate piece 10 thus includes the pair of legs 15, 16 and the gradation 11.

In the occluder 7 illustrated in FIG. 3 the legs 20, 21 of both closure bodies 8, 9 are connected to one another electrically conductively in the vicinity of the gradation 11, whereby the legs 20, 21 are connected solidly by a ceramic sleeve 22, ensuring a dimensionally stable arrangement of the occluder 7. With the exception of the gradation 11 the legs 20, 21 are, however, not connected and can be bent so that the annular closure bodies 8, 9 formed by the wire 17 can adapt easily to an enclosing body wall.

FIGS. 4 to 7 in each case illustrate an occluder 7 which forms an electric oscillating resonance circuit. The occluder 7 is again respectively formed by a one-piece wire 17, whereby the wire 17 constitutes a conductive loop of the oscillating resonance circuit and forms inductivity. The conductive loop has two windings in the form of the closure bodies 8, 9 formed as a wire ring. In addition, the conductive loop or respectively the wire 17 forms capacitance of the oscillating resonance circuit, whereby according to the embodiments illustrated in FIGS. 4 to 7 the wire ends 23, 24 of the wire 17 are guided over a preset distance parallel to one another and are arranged spaced apart. Formed between the wire ends 23, 24 is a dielectric. By way of example, it can be provided that the wire ends 23, 24 are stuck together using a non-conductive adhesive.

With the occluder 7 illustrated in FIG. 3 the gradation 11 of the intermediate piece 10 is arranged substantially at a right angle to the pairs of legs 15, 16. In the embodiment illustrated in FIG. 6 the occluder 7 on the other hand has an intermediate piece 10 with an obliquely positioned gradation 11. This facilitates complete sealing of the body orifice 6 after the occluder 7 is inserted through the closure bodies 8, 9.

Figure 5:
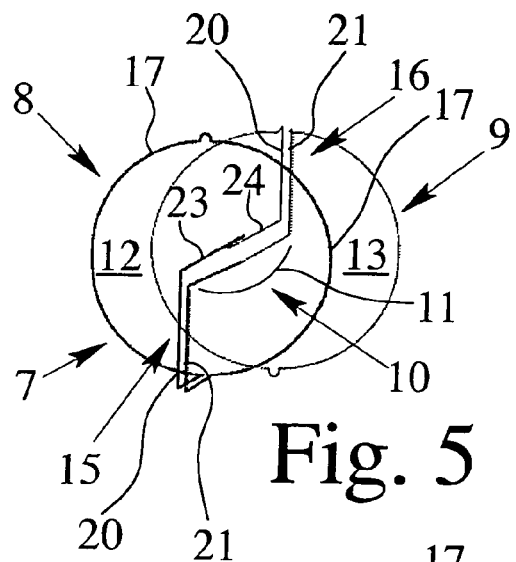
FIG. 5 shows a schematic plan view of a third embodiment of an inventive occluder.

FIG. 5 illustrates an embodiment of an occluder 7, wherein the legs 20, 21 of the pair of legs 15, 16 are arranged outside the closure surfaces 12, 13. For this it is provided that the wire sections 18, 19 forming the wire ring of the closure bodies 8, 9 and converging towards one another are angled in an axial direction and outside the closure surface 12, 13 are bent in the direction of the central point of the wire ring. The gradation 11 is guided in through the closure surfaces 12, 13 of the closure bodies 8, 9. It can just as well be provided that the legs 20, 21 are angled relative to the closure surfaces 12, 13 such that the legs 20, 21 cannot lead to interruption to the inductivity of the oscillating resonance circuit.

Figure 6:
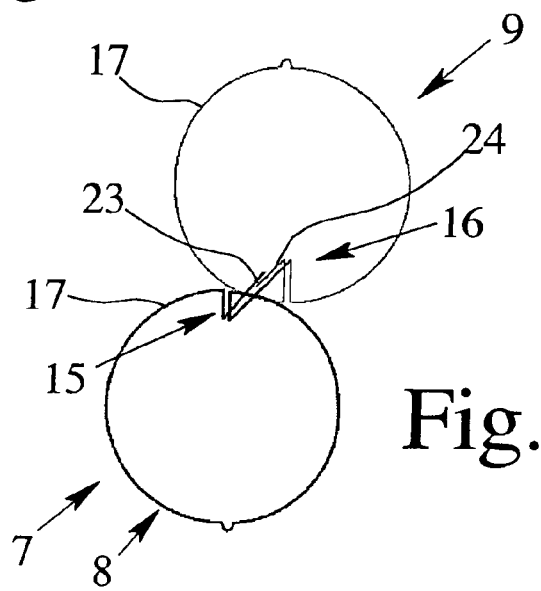
FIG. 6 shows a schematic plan view of a fourth embodiment of an inventive occluder.

FIG. 6 illustrates an embodiment of an occluder 7, in which the closure bodies 8, 9 are offset to one another transversely to the direction of sealing. This asymmetrical arrangement of the closure bodies 8, 9 enables easy sealing of the body orifice 6, whereby the closure bodies 8, 9 cover one another to a minimal degree only. This is adequate, however, to guarantee sealing of the body orifice 6. The degree of overlap of the closure bodies 8, 9 is determined by the length of the pair of legs 15, 16.

Figure 7:
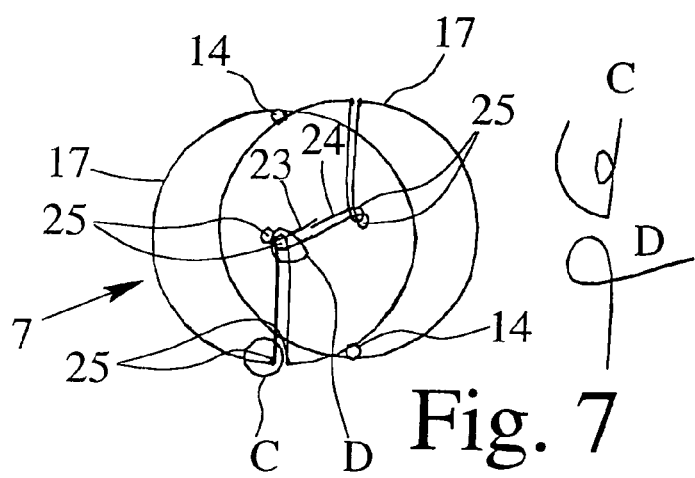
FIG. 7 shows a schematic plan view of a fifth embodiment of an inventive occluder.

FIG. 7 shows that the occluder 7 can have a plurality of torsion springs 25 which facilitate combining the occluder 7 by stretching in a longitudinal direction and can serve as an application section for an implant instrument. In addition, the torsion springs 25 contribute to considerable dimensional stability of the occluder 7. Not illustrated is that a torsion spring 25 can also be provided in the vicinity of the gradation 11 of the intermediate piece 10. At the same time the leg area framed by the torsion spring 25 can preferably be arranged parallel to the closure surfaces framed by the closure bodies 8,9. In this case the torsion spring 25 can contribute to anchoring the occluder 7 in the defect. Also, the intermediate piece 10 can have any form, for example tapering in the middle region, to improve centring of the occluder 7 in the defect. The intermediate piece 10 can also be formed to contribute to sealing of the defect. For anchoring with the defective wall parts in the vicinity of the orifice 6, 6a the intermediate piece 10 of any form can have outlying cogging which cooperates with the defective wall parts in the implanted state of the occluder 7. Further, the occluder 7 illustrated in FIG. 7 has an eyelet-shaped application section 14 for a guide wire which makes it easier to thread the occluder 7 into a body orifice 6.

FIGS. 8 and 9 illustrate in detail that the conductive loop of the occluder 7 can form capacitance of the oscillating resonance circuit. As per FIG. 8 opposite plates 26 are attached in the vicinity of the gradation 11 to the wire ends 23, 24 such that the capacitance belonging to the oscillating resonance circuit is made in the form of a plate condenser. A dielectric region 27 is provided between the platelet 26. The wire ends 23, 24 and the leg 21 formed from the wire 17 are enclosed by a plastic sleeve 28. Not illustrated is that the plastic sleeve 28 can have a guide aperture for a guide wire. The embodiment in FIG. 9 schematically illustrates that capacitance of the oscillating resonance circuit formed by the occluder 7 can be formed in certain areas by wire ends 23, 24 guided parallel to one another. Provided between the wire ends 23, 24 is again a dielectric region 27.

Figure 11:
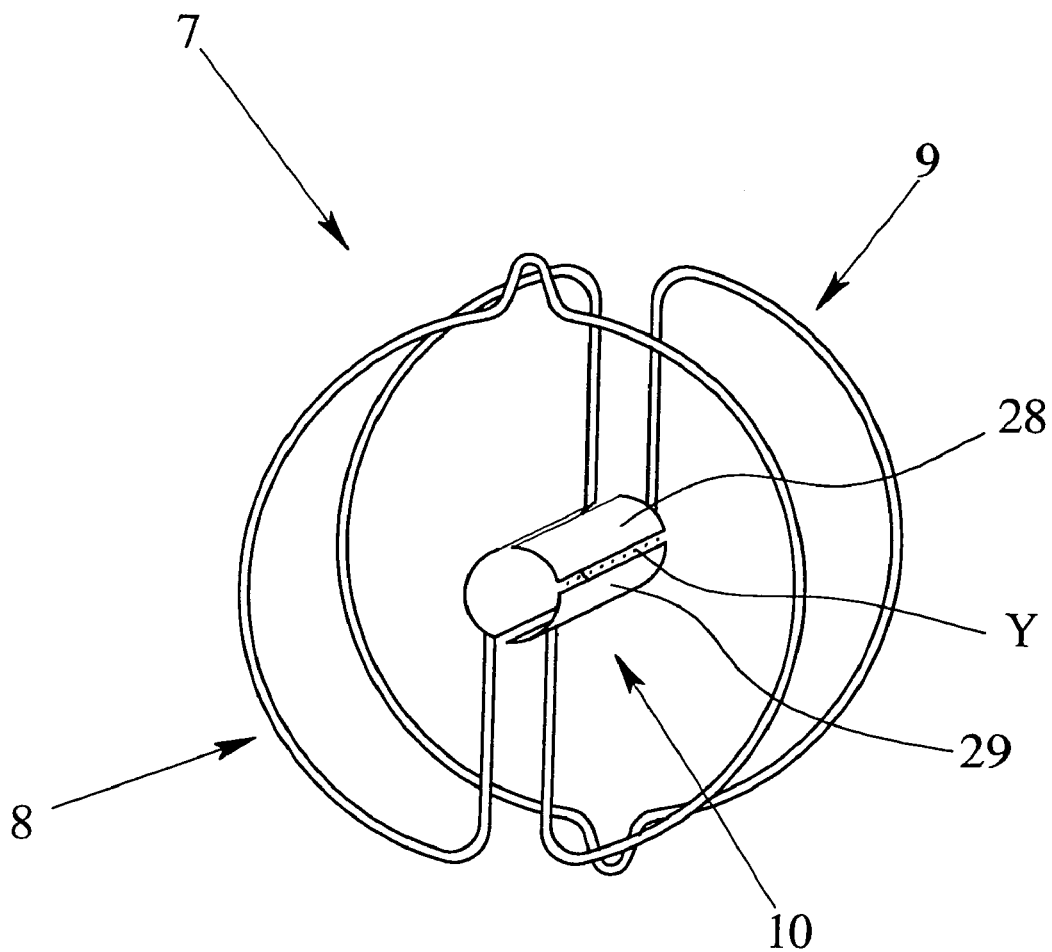
FIG. 11 shows a schematic illustration of areas forming capacitance of the intermediate part of an occluder.

The occluder 7 can be produced by repeated lengthways cutting of a pipe, in particular a nitinol pipe, and subsequent expansion. FIG. 11 illustrates an embodiment of an occluder 7 cut fully from a nitinol pipe after bending, whereby capacitance can be made between the part areas 28, 29 of the intermediate piece 10 by appropriate forming of the intermediate piece 10. The capacitance to be produced is illustrated schematically by a dotted line Y.

Not illustrated is that during production of the occluder 7 the conductor sections forming the occluder 7 can be connected to one another in the vicinity of the intermediate piece 10 first by bridging so as to fix the conductive pieces in the vicinity of the intermediate piece 10 at a specific distance from one another. Next, the conductive pieces are embedded in the vicinity of the intermediate piece 10 in an embedding mass. After curing of the embedding mass the bridges are then disconnected, whereby the conductive pieces have a defined distance for forming capacitance, in the embedded state.

The occluder 7 is then embedded in the vicinity of the intermediate piece 10 in an embedding mass. This fixes the conductive pieces in the vicinity of the intermediate piece 10 relative to one another such that the bridges between the conductive pieces can then be dissolved. Next, the heating and deforming of the conductive pieces is provided when the occluder 7 is manufactured.

Figure 12:
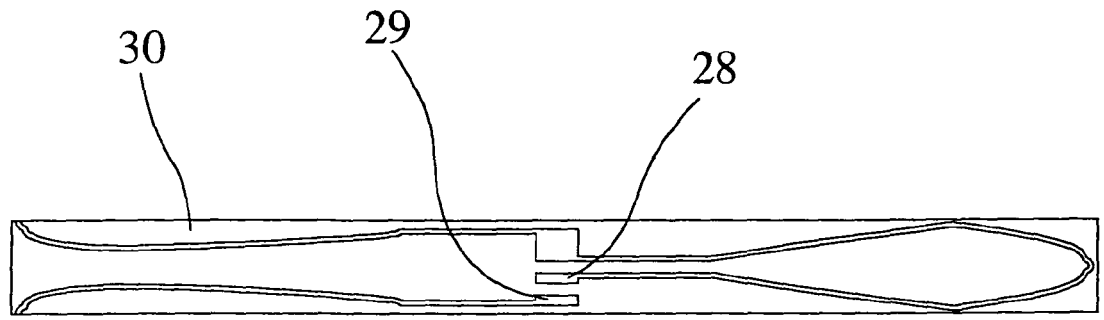
FIGS. 12-14 show possible cutting patterns of a pipe for making a conductive loop of an occluder.
Figure 13:
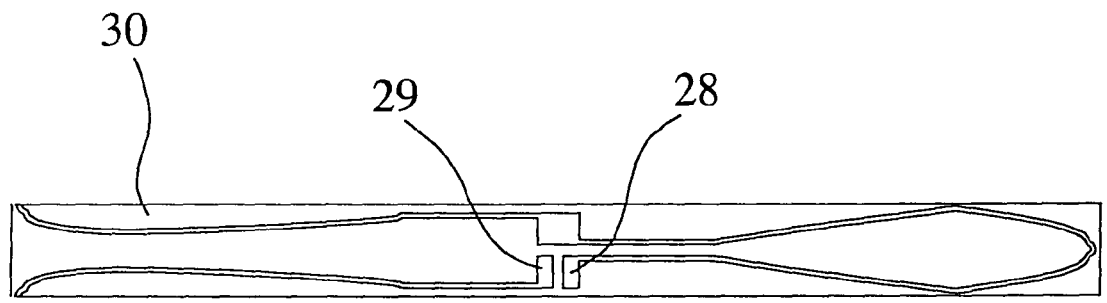
Figure 14:
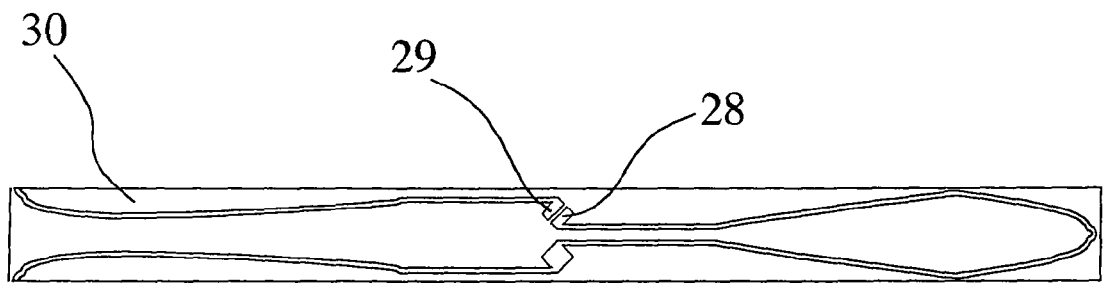
Figure 15:
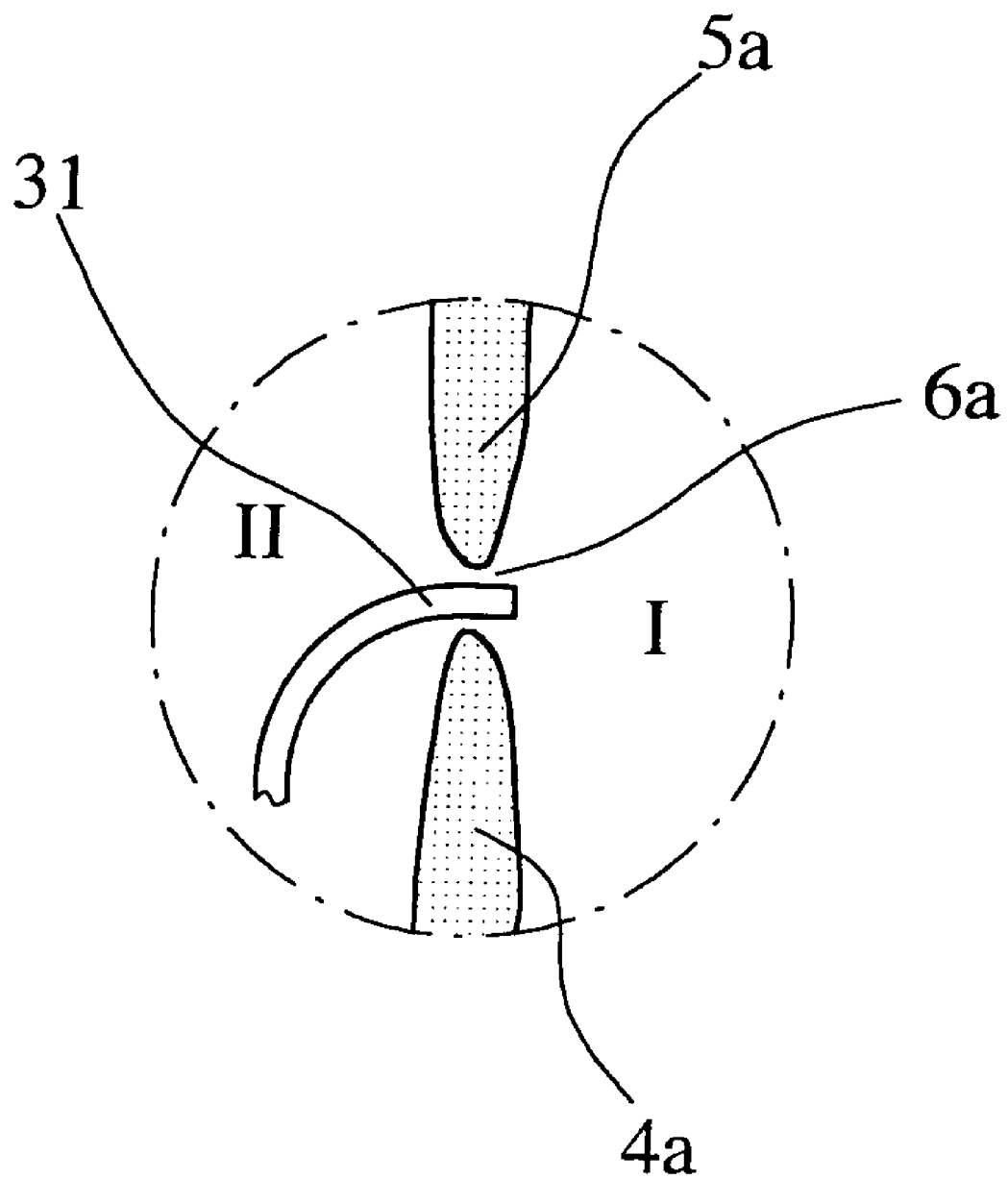
FIGS. 15-22 show a schematic illustration of the implant procedure of an occluder for sealing the wall defect illustrated in FIG. 2, and FIGS. 23-27 show another embodiment of an occluder.
Figure 16:
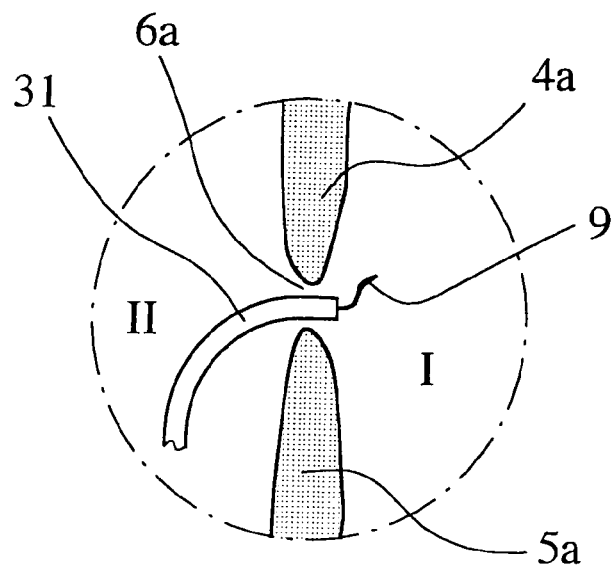
Figure 17:
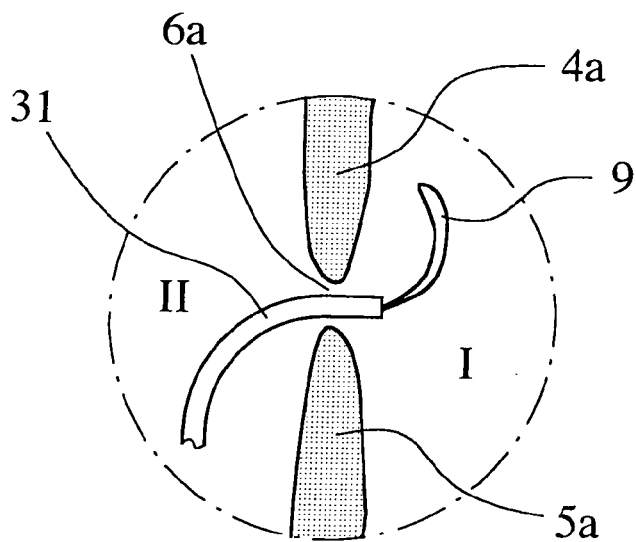
Figure 18:
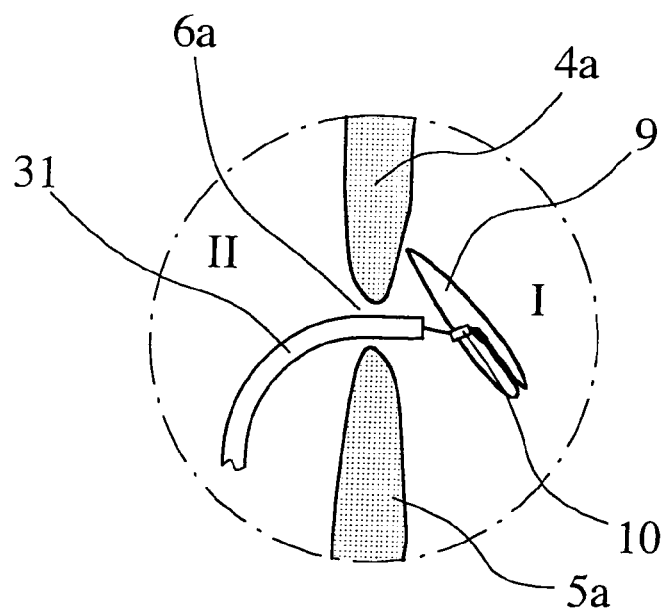

FIGS. 12 to 14 illustrate cutting patterns of a pipe 30 for alternative embodiments of an occluder 7, with capacitance-forming areas 28, 29 provided and arranged variously in the vicinity of the intermediate piece 10. The pipe 30 is preferably a nitinol pipe with an outer diameter of 1 to 3 mm, in particular of 2 mm, and a wall thickness of 0.4 to 0.6 mm, in particular 0.2 mm. The conductive piece cut from the pipe 30 is preferably gilded, whereby the gap provided between the capacitance-forming areas 28, 29 may not be closed during the gilded procedure. The occluder 7 can be fixed by means of plastic, for example epoxy resin, in the region of the intermediate piece 10 resulting in a stable ring which forms unalterable capacitance and possibly can be used as a guide for a guide wire.

Figure 19:
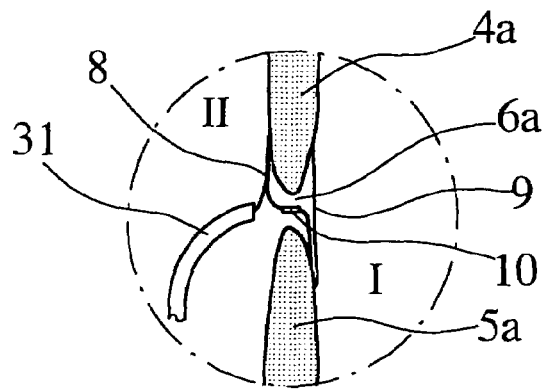
Figure 20:
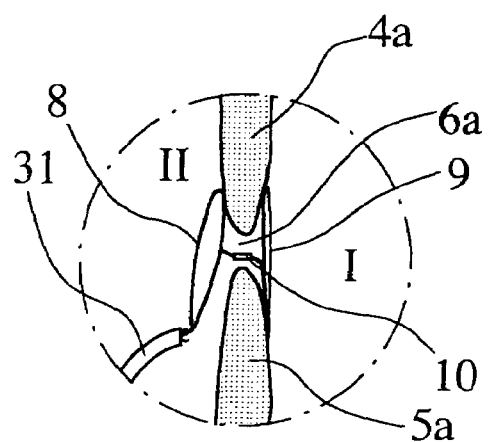
Figure 21:
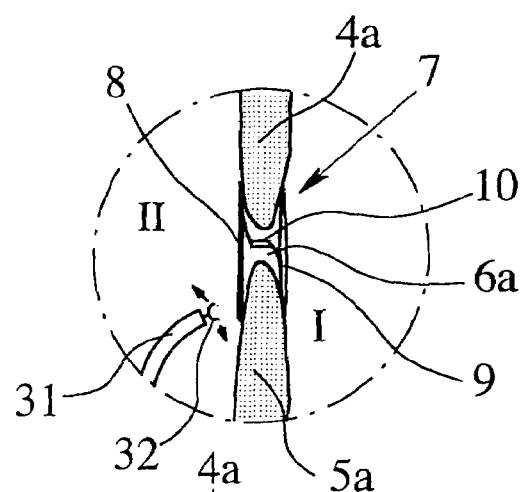
Figure 22:
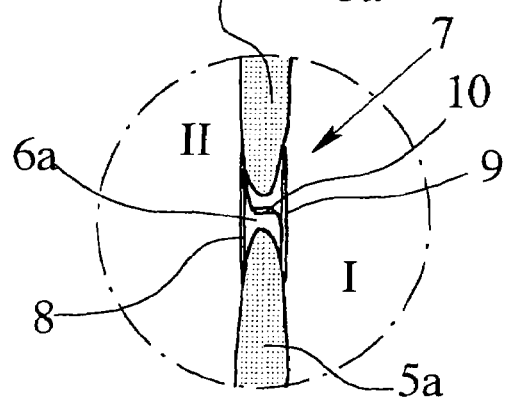
Figure 23:
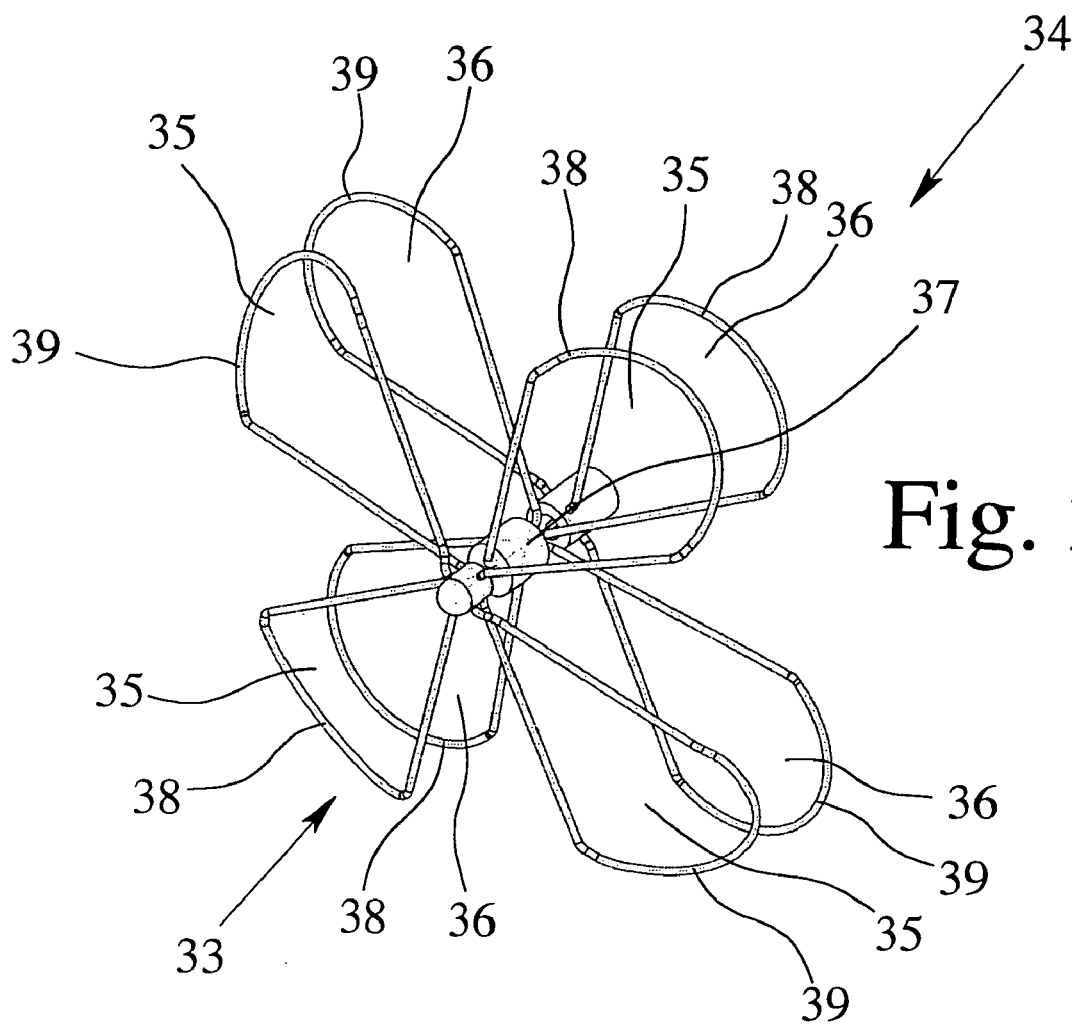
Figure 24:
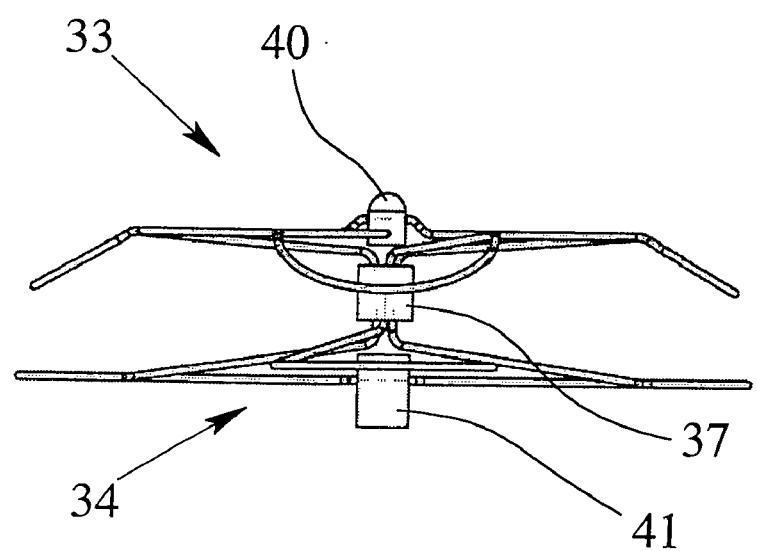

The procedure for implanting an occluder 7 into the body orifice 6a illustrated in FIG. 2 is explained schematically by way of FIGS. 15 to 22, whereby the body orifice 6a is delimited by two defective wall parts 4a, 5a. The occluder 7 is fed in via a catheter 31, whereby the free end of the catheter 31 is positioned in through the body orifice 6a onto the one side I of the wall defect. FIGS. 16 to 19 show the release and unfolding of the proximal closure body 9 on the side I of the wall defect. FIG. 19 shows the application of the closure body 9 to the defective wall parts 4a, 5a on the side I of the wall defect and the release of the intermediate piece 10 as well as the distal closure body 8 of the occluder 7 freed by withdrawing the partly freed catheter 31 on the other side II of the body orifice 6a. Further withdrawal of the catheter 31 results in complete release of the distal closure body 8, as illustrated in FIGS. 20 and 21. Opening a gripping mechanism 32 of the catheter 31 results in release of the occluder 7, whereby the occluder 7 is illustrated in the fully unfolded state in FIG. 22. The closure bodies 8, 9 are pressed by the intermediate piece 10 on both sides I, II of the wall defect against the defective wall parts 4a, 5a, leading to sealing the body orifice 6a by tissue growth in this area.

Figure 25:
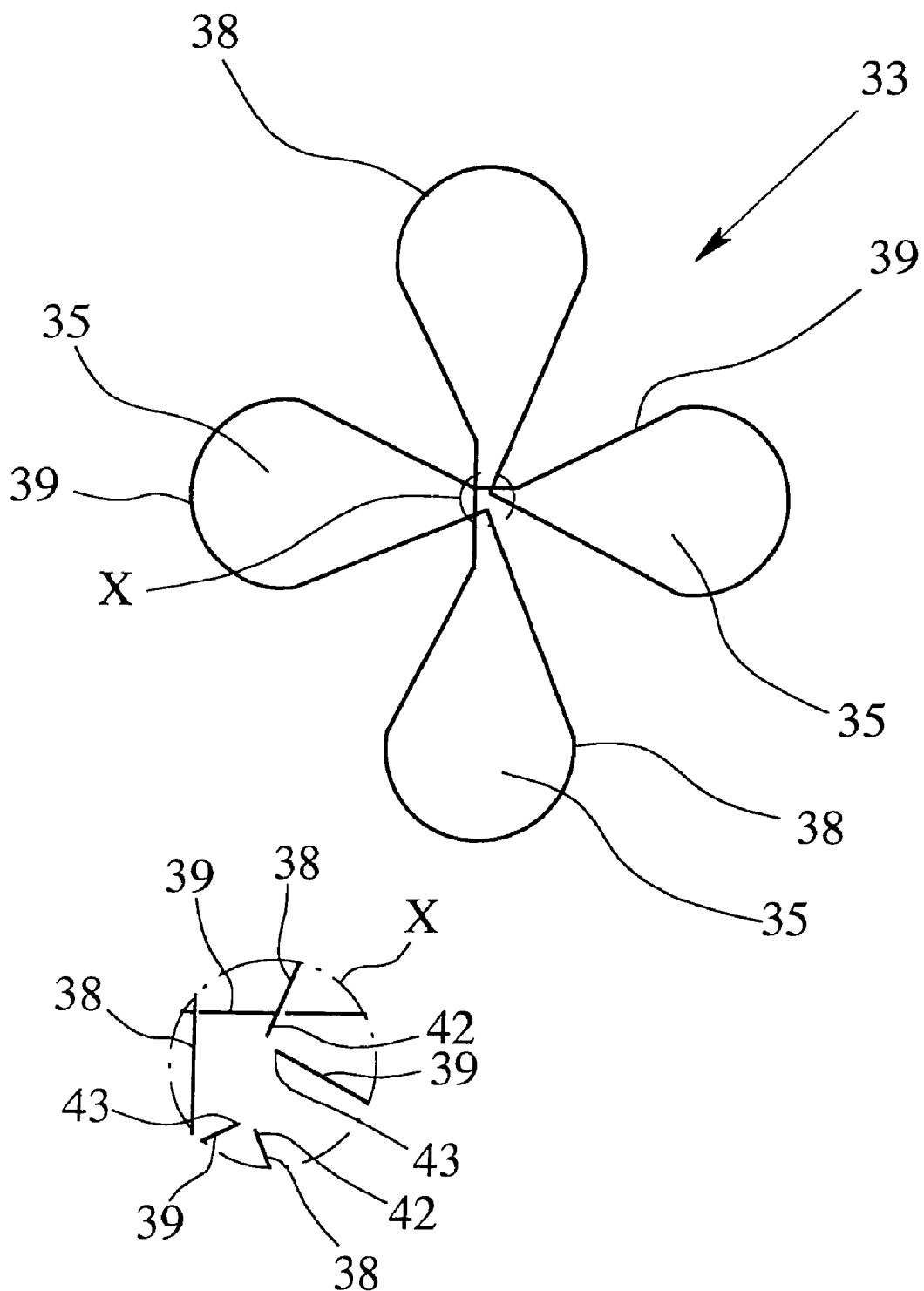

A further embodiment of an occluder 7, which has an upper shield-like closure body 33 and a lower shield-like closure body 34, is described by means of FIGS. 23 to 27. The closure bodies 33, 34 are formed in each case by four segments 35, 36. The closure bodies 33, 34 are connected to one another by an intermediate piece 37. The segments 35, 36 of the closure body 33, 34 are in each case formed by two wire pieces 38, 39, as illustrated in FIG. 25 by way of example for the upper closure body 33. A wire piece 38 or respectively 39 in each case forms two opposite segments 35. The segments 36 of the lower closure body 34 are likewise formed by two wire pieces 38, 39.

For connecting the wire pieces 38, 39 of the upper closure body 33 an upper connecting piece 40 is provided and for connecting the wire pieces 38, 39 of the lower closure body 34 a lower connecting piece 41 is provided. The connecting pieces 40, 41 and the intermediate piece 37 can be designed as capacitance. In addition, the required capacitance can be provided in the form of an additional condenser component which is attached between adjacent wire ends 42, 43 of the wire pieces 38, 39 of the upper closure body 33 and of the lower closure body 34, not however illustrated in detail. In addition, it is possible to design the capacitance preferably by arranging the adjacent wire ends 42, 43 of the wire pieces 38, 39 of a closure body 33, 34 at a defined distance from one another. This is illustrated by way of example for the upper closure body 33 in FIG. 25 by means of the detail X. Here it is possible for the wire ends 42, 43 to be arranged parallel to one another.

Figure 26:
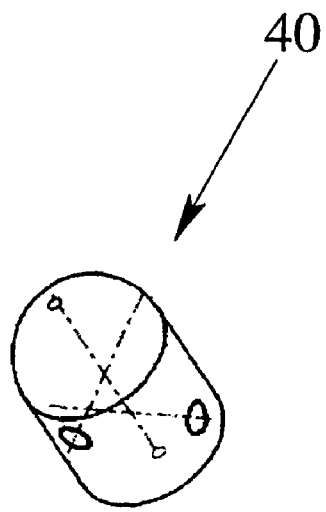
Figure 27:
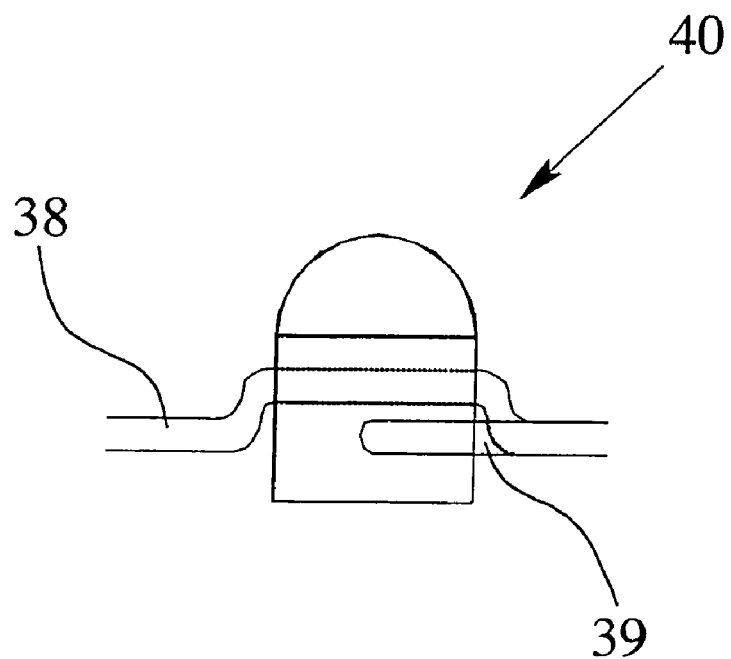

The connecting piece 40 for the wire pieces 38, 39 of the upper closure body 33 is illustrated in FIGS. 26 and 27. FIG. 27 illustrates the course of the wire pieces 38, 39 through the connecting piece 40. The wire pieces 38, 39 are in the process fixed by being guided in the connecting piece 40. Also, the wire ends 42, 43 of the wire pieces 38, 39 are fixed in the intermediate piece 37, as evident from FIG. 24.

The invention claimed is:

1. An occluder for sealing a body orifice of the human or animal body, comprising at least one conductive loop forming an inductivity of an electric oscillating resonance circuit, wherein the occluder or parts of the occluder form the electric oscillating resonance circuit and the occluder or parts of the occluder are formed by the conductive loop, wherein the conductive loop forms a capacitance of the oscillating resonance circuit and a condenser is made by parallel sections of the conductive loop, wherein the occluder further comprises at least two opposite closure bodies arranged at least in certain areas on opposite sides of the body orifice in the state of closure of the body orifice and at least one intermediate piece joining together the closure bodies, whereby the intermediate piece at least in certain areas is guided in through the body orifice in the state of closure, wherein the closure bodies are formed by the conductive loop and wherein the closure bodies form the inductivity and the intermediate piece forms the capacitance of the oscillating resonance circuit.

2. The occluder according to claim 1, further comprising
a one-sided connection is provided between the intermediate piece and each closure body,
whereby the intermediate piece is connected eccentrically to each closure body in the edge region of the closure body in the state of closure and whereby the opposite closure bodies in the state of closure arranged on opposite sides of the body orifice are connected on opposite sides (A, B) to the intermediate piece.

3. The occluder according to claim 2, wherein the intermediate piece has a gradation with at least two opposing legs, whereby each leg is connected by its free end to a closure body.

4. The occluder according to claim 3, wherein the legs of the intermediate piece have the same length such that in the state of closure the gradation is arranged substantially centrically to the closure bodies arranged on opposite sides of the body orifice.

5. The occluder according to claim 2, wherein in the state of closure the closure bodies arranged on opposite sides of the body orifice substantially overlap one another.

6. The occluder according to claim 2, wherein the closure bodies and the intermediate piece are formed from a one-piece wire made of shape memory alloy or cut from a pipe made of shape memory alloy.

7. The occluder according to claim 2, wherein the occluder is formed by a one-piece wire converging at its ends, whereby the wire is deformed at opposite points in each case into a wire ring forming an outer closure body, whereby the wire ring has two converging wire sections, whereby the wire sections are bent radially in the direction of the midpoint of the wire ring and merge into legs running parallel to one another and whereby the legs of both closure bodies form the inner intermediate piece.

8. The occluder according to claim 2, wherein the legs of both closure bodies are connected to one another in the vicinity of the intermediate piece, in particular in the vicinity of the gradation.

9. The occluder according to claim 2, wherein the ends of a wire form a condenser of the oscillating resonance circuit.

10. The occluder according to claim 2, wherein the closure body spans a closure surface and that the legs forming the intermediate piece are arranged to run outside the closure surface.

11. The occluder according to claim 2, wherein the intermediate piece and/or the occluder and/or at least one of the closure bodies, are encased in tissue.

12. The occluder according to claim 2, wherein the intermediate piece is encased in the vicinity of the gradation with a sheathing and that the sheathing optionally has a guide aperture for a guide wire.

13. The occluder according to claim 2, wherein the occluder has at least one hook-shaped or eyelet-shaped application section for an implant instrument.

14. The occluder according to claim 2, wherein the wire is formed on at least one folding or bending point as a torsion spring.

15. The occluder according to claim 2, wherein the intermediate piece has a shape for sealing the body orifice and/or for centering and/or for anchoring the occluder in the body orifice.

16. The occluder according to claim 2, wherein the intermediate piece has at least one torsion spring, whereby another closure surface is optionally stretched by the torsion spring, which is arranged substantially parallel to a closure surface stretched by the closure body.

* * * * *